United States Patent [19]

Weitz et al.

[11] 4,060,543
[45] Nov. 29, 1977

[54] MANUFACTURE OF 5-CYANOVALERIC ACID AND ITS ESTERS

[75] Inventors: Hans-Martin Weitz, Bad Durkheim; Rolf Fischer, Heidelberg, both of Germany

[73] Assignee: BASF Aktiengesellschaft, Ludwigshafen, Germany

[21] Appl. No.: 710,427

[22] Filed: Aug. 2, 1976

[30] Foreign Application Priority Data

Sept. 18, 1975  Germany .......................... 2541640

[51] Int. Cl.$^2$ .......................................... C07C 120/00
[52] U.S. Cl. ............................ 260/464; 260/465 D; 260/465.4
[58] Field of Search .............. 260/465.4, 465 D, 464

[56] References Cited

U.S. PATENT DOCUMENTS

| | | | |
|---|---|---|---|
| 2,506,571 | 5/1950 | Barrick | 260/465.6 |
| 3,116,306 | 12/1963 | Heck et al. | 260/465.4 X |
| 3,210,400 | 10/1965 | Brakebill | 260/465.4 |
| 3,337,603 | 8/1967 | Kato et al. | 260/465.6 X |
| 3,437,676 | 4/1969 | von Kutepow | 260/465.4 X |

OTHER PUBLICATIONS

Matsuda, Bull. Chem. Soc. Japan, 40 (1967), pp. 135–144.

*Primary Examiner*—Joseph Paul Brust
*Attorney, Agent, or Firm*—Keil, Thompson & Shurtleff

[57] ABSTRACT

5-Cyanovaleric acid and its esters are manufactured by reacting pentenonitriles with water or alcohols and carbon monoxide in the presence of metal carbonyls and heterocyclic compounds at elevated temperature under pressure. 5-Cyanovaleric acid and its esters are starting materials for the manufacture of dyes, pesticides, fibers, especially nylon fibers, and plastics.

9 Claims, No Drawings

MANUFACTURE OF 5-CYANOVALERIC ACID AND ITS ESTERS

The present invention relates to a process for the manufacture of 5-cyanovaleric acid and its esters by reacting pentenonitriles with water or alcohols and carbon monoxide in the presence of metal carbonyls and heterocyclic compounds at elevated temperature under pressure.

Bull.Chem.Soc. Japan, 40 (1967), 135–144, discloses that acrylonitrile can be reacted with carbon monoxide and methanol in the presence of cobalt carbonyl, pyridine and hydrogen, essentially to give α-cyanopropionic acid methyl esters. According to the disclosure of this publication, temperatures of from 84° to 124° C must be used. The presence of a certain amount of hydrogen is essential for carrying out the reaction. The publication shows that a mixture of α- and β-cyanopropionate in the ratio of 1:1 is obtained if no pyridine is added. Only in the case of such mixtures is a relatively large amount of the β-component obtained at all; in the presence of pyridine, the β-component always remains only a by-product. According to the stated experimental conditions, the ratio of α-component to β-component increases with increasing pressure; pressures of from 60 to 190 kg/cm² are mentioned. If the hydrogen partial pressure is increased, the ratio of α-component to β-component decreases.

Annalen der Chemie, 596 (1955), 127, discloses that 5-cyanovaleric acid can be obtained by heating 5-valerolactone and sodium cyanide, and can be converted to the corresponding esters by reaction with alcohols. The process is unsatisfactory in respect of simple, reliable and economical operation and in respect of yield and purity of the end product.

It is an object of the present invention to provide a new process for the simpler and more economical manufacture of 5-cyanovaleric acid and its esters in better yield and higher purity, especially on an industrial scale.

We have found that this object is achieved and that 5-cyanovaleric acid and its esters are obtained in an advantageous manner by reaction of alkenyl-nitriles with carbon monoxide and hydroxyl-containing compounds at elevated temperature and elevated pressure, in the presence of metal carbonyls and basic compounds, when a pentenonitrile of the formula

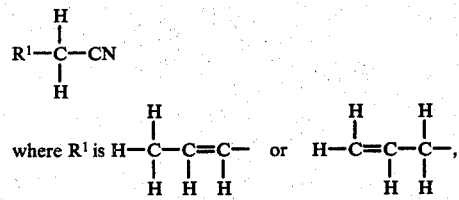

is reacted with carbon monoxide and compounds, containing a hydroxyl group, of the formula $$R^2\text{---OH} \qquad \qquad II$$

where R² is an aliphatic, cycloaliphatic, araliphatic or aromatic radical or a hydrogen atom, at not less than 140° C and a pressure of not less than 100 bars, in the presence of metal carbonyls and basic heterocyclic compounds having a 5-membered or 6-membered nitrogen-containing ring.

Further, we have found that the process can be carried out advantageously by effecting the reaction without added hydrogen.

Where 3-pentenonitrile and methanol are used, the reaction can be represented by the following equation:

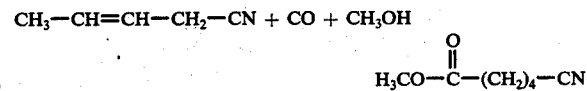

Compared to the prior art, the process according to the invention gives 5-cyanovaleric acid and its esters by a simpler and more economical method and in better yield and higher purity, especially on an industrial scale. Toxic compounds which are difficult to handle industrially, such as sodium cyanide, are avoided; the process causes less polution of the environment. A separate esterification operation is no longer needed. All these advantageous results are surprising in view of the prior art. Instead, a substantial yield of 2-methyl-4-cyanobutryic acid or 2-methyl-4-cyanobutyric acid methyl ester, and the formation of carboxylic acid amides and carboxylic acid esters, or at least of mixtures of numerous components as end products would have been expected.

3-Pentenonitrile which is preferentially used for the manufacture of 5-cyanovaleric acid or its esters can be manufactured by addition reaction of hydrocyanic acid with butadiene, for example in the presence of nickel-containing complex compounds or of copper-(I) chloride, in accordance with the process disclosed in German Laid-Open Applications DOS NOs. 15 93 277, 23 44 767 and 20 09 470. 4-Pentenonitrile, or mixtures of the said pentenonitriles, which in addition can contain 2-pentenonitrile, can also be used as starting materials for the carbonylation.

Preferred compounds II and, accordingly, preferred end products of the formula

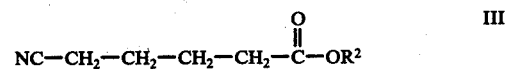

are those where R² is alkyl of 1 to 12 carbon atoms, especially of 1 to 8 carbon atoms, which may or may not be substituted by 1 or 2 hydroxyl groups, cycloalkyl of 5 to 7 carbon atoms, aralkyl of 7 to 12 carbon atoms, phenyl or hydrogen. The above radicals may further be substituted by groups which are inert under the reaction conditions, eg. alkyl or alkoxy each of 1 to 4 carbon atoms, or hydroxyl.

Examples of suitable alcohols II are methanol, isopropanol, ethanol, dodecanol, n-propanol, tert.-butanol, nonanol, sec.-butanol, n-hexanol, n-butanol, iso-butanol, 2-ethylhexanol, cyclohexanol, benzyl alcohol, ethylene glycol, methylglycol, 1,3-propanediol, 1,4-butanediol, 1,2-propanediol, neopentylglycol, 2,4-pentylene glycol, 2,3-butylene glycol, 1,6-hexanediol, cyclopentanol, cycloheptanol, phenylethyl alcohol, n-pentanol, phenylpropanol, phenol, cyclooctanol, n-heptanol, n-octanol, n-decanol, 2-methylphenol, 3-methylphenol, 4-methylphenol, 2-methoxyphenol, 3-methoxyphenol, 4-methoxyphenol, 2,3-dimethylphenyol, 3,4-dimethylphenol, 2,6-dimethylphenol, 3,5-dimethylphenol, 2,3-dimethoxyphenol, 3,4-dimethoxyphenol, 3,5-dimethoxyphenol, 2-ethylphenol, 3-ethylphenol, 4-ethylphenol, 2,3-diethylphenol, 3,4-diethylphenol, 2,6-diethylphenol, 3,5-diethylphenol, 2-ethoxyphenol, 3-ethoxyphenol, 4- ethoxyphenol, 2-n-propylphenol, 3-n-propylphenol, 4-n-propylphenol, 2,3-di-n-propylphenol, 3,4-di-n-propylphenol, 2,6-di-n-propylphenol, 3,5-di-n-propylphenol, 2-isopropylphenol, 3-isopropylphenol, 4-isopropylphenol, 2-butylphenol, 3-butylphenol, 4-butylphenol, 2-isobutylphenol, 3-isobutylphenol, 4-isobutylphenol, 2-tert.-butylphenol, 3-tert.-butylphenol, 4-tert.-butylphenol, 2,3-diethoxyphenol, 3,4-diethoxyphenol, 2,6-diethoxyphenol and 3,5-diethoxyphenol.

Water, or the alcohols II, can be used in the reaction in the stoichiometric amount or in an excess, preferably in a ratio of from 1 to 10 moles of water or alcohol II per mole of pentenonitrile I. Mixtures of water and alcohols can also be used.

If excess starting material I is used in the case of polyhydroxyalcohols, corresponding diesters or polyesters of 5-cyanovaleric acid are formed. The alcohol or water required for the reaction can at the same time also serve as the solvent, in which case the amount is advantageously from 10 to 50 moles of water or alcohol II per mole of starting material I. If appropriate, organic solvents which are inert under the reaction conditions can also be used, such as aromatic hydrocarbons, eg. benzene, toluene, ethylbenzene, o-xylene, m-xylene, p-xylene, isopropylbenzene and methylnaphthalene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether, ketones, such as methyl ethyl ketone, acetone, diisopropyl ketone, diethyl ketone, acetophenone and cyclohexanone, and appropriate mixtures, including mixtures with water. Advantageously, the amount of solvent used is from 1 to 15 moles, preferably from 2 to 10 moles, per mole of starting material I. The reaction is in general carried out at from 140° to 300° C, preferably from 140 to 250° C, especially from 150° to 200° C, under pressure, as a rule from 100 to 700 bars, advantageously from 160 to 300 bars and especially from 200 to 300 bars, continuously or batchwise. If the reaction is carried out at from 100° to 140° C, substantially poorer yields of end product are obtained.

Carbon monoxide can be employed in the stoichiometric amount or in excess, preferably in an amount of from 10 to 50 moles, especially from 20 to 30 moles, of carbon monoxide per mole of starting material I. As a rule, the process is advantageously carried out without added hydrogen or in a reaction medium which is free from hydrogen; minor amounts of hydrogen, which are entrained by the reactants, eg. by the carbon monoxide, or are formed during the reaction, eg. from carbon monoxide and water, can be present.

The reaction is carried out in the presence of basic heterocyclic compounds having a 5-membered or 6-membered nitrogen-containing ring. Preferred heterocyclic compounds are 5-membered or 6-membered heterocyclic rings which are unsubstituted or substituted by alkyl or alkoxy each of 1 to 4 carbon atoms, or by hydroxyl, to each of which heterocyclic rings one or 2 aromatic nuclei, which may be unsubstituted or substituted by the above substituents, may be fused; amongst the fused-ring compounds, those with only one fused nucleus are preferred. Preferred heterocyclic rings in particular only contain one nitrogen atom as the heteroatom, but may also contain a further nitrogen atom or an oxygen atom, and furthermore contain 2 or 3 double bonds. Amounts of from 0.1 to 2 moles, preferably from 0.1 to 1 mole, of heterocyclic compound may be used per mole of starting material I.

Examples of preferred heterocyclic compounds are quinoline, isoquinoline, imidazole, 1-methylimidazole, 1-propylimidazole, 2-methylpyridine, 3-methylpyridine, 4-methylpyridine, 2,4-dimethylpyridine, 2,6-dimethylpyridine, 2,4,6-trimethylpyridine and especially pyridine; however, pyrrolidine, $\Delta^1$-pyrroline, $\Delta^2$-pyrroline, $\Delta^3$-pyrroline, $\alpha$-pyrrolenine, $\beta$-pyrrolenine, pyrrole, isooxazole, oxazole, pyrazole, pyrazoline, pyrazolidine, imidazolidine, 3-imidazoline, 2,3,4,5-tetrahydropyridine, pyridazine, pyrimidine, pyrazine, piperazine, indoline, indole, 2-H-indole, indolenine, isoindoline, isoindole, indolizidine, benzoxazole, indazole, benzimidazole, 1,2,3,4-tetrahydroisoquinoline, cinnoline, quinazoline, quinoxaline, phthalazine, carbazole, acridine, phenoxazine, phenazine, 4-methoxypuridine, -methoxypyridine, 2-methylbenzoxazole, 2-methylquinoline, 4-methylimidazole, 1-methylindole, 2-methylindole, 3-methylindole, 3-methylisoquinoline, 2-methylpiperazine, 2-methylpyrazine, 3-methylpyrrole, 2-methylpyrrole and 2-ethylpyridine can also be used.

Suitable metal carbonyls are pure carbonyls, carbonyls of which the carbon monoxide is partially replaced by neutral or charged ligands, and carbonyl hydrides, advantageously those of iridium, iron, nickel, ruthenium, rhodium and, particularly preferentially, cobalt. Regarding the manufacture of the carbonyls, reference may be made to Ullmanns Encyklopaedie der technischen Chemie, volume 12, pages 312-324. Instead of the above carbonyls, the corresponding metals or metal compounds which are able to form such carbonyls under the reaction conditions can also be used. Advantageous metal compounds to use are the halides, especially iodides and chlorides, acetates, oxides and sulfates of the above metals, eg. cobalt acetate tetrahydrate. Examples of substituents which may be present in the substituted carbonyls are trialkyl compounds, triaryl compounds and trihalides or phosphorus, amines, isonitriles and cyanide ions, and halogens, eg. in the form of carbonyl halides, such as chlorides or iodides. Advantageously, from 0.005 to 0.1, preferably from 0.01 to 0.05, mole of carbonyl compound is used per mole of starting material I.

Examples of metal carbonyls and derivatives of metal carbonyls which can be used are $Fe(CO)_5$, $Ni(CO)_4$, $Ru(CO)_5$, $Rh_2(CO)_8$, $Ir_2(CO)_8$, $((C_6H_5)_3P)_2Ni(CO)_2$, $((C_6H_5)_3P)Fe(CO)_4$, $Ni(CN-C_6H_5)_4$, $K_2[Ni(CO)_2(CN)_2]$, $Ir(CO)_2Br_2$, $HCo(CO)_4$, $H_2Fe(CO)_4$, $HRh(CO)_4$ and preferably dicobaltoctacarbonyl $Co_2(CO)_8$.

The reaction can be carried out as follows: a mixture of the starting materials I and II, carbon monoxide, the base and the metal carbonyl, with or without a solvent, is kept at the reaction temperature and the reaction pressure for from 1 to 20 hours. Advantageously, a mixture of pentenonitrile I, water or alcohol II, base and metal carbonyl, in a suitable solvent, is first introduced into a reactor filled with nitrogen or argon. After forcing carbon monoxide at room temperature into the reactor, the mixture is raised to the reaction temperature. If necessary, further carbon monoxide is then forced in, to reach the reaction pressure. The reaction is now advantageously carried out for from 1 to 20 hours under the stated conditions, after which the mixture is cooled and the pressure is let down. The end product is now isolated from the mixture in the conventional manner, eg. by fractional distillation. Depending on its boiling point, the heterocyclic compound either remains in the distillation residue or distils off. After the distillation, cobalt carbonyl remains in the residue, and the latter can, if necessary after addition of base, be used for further carbonylation reactions without significant reduction in yield.

5-Cyanovaleric acid and its esters are valuable starting materials for the manufacture of dyes, pesticides, fibers, especially nylon fibers, and plastics. Caprolactam is obtained by hydrogenating them to give 6-aminocaproic acid or 6-aminocaproic acid esters, respectively, and eliminating the water or alcohol. Regarding their use, reference may be made to the cited publications and to Ullmanns Encyklopaedie der technischen Chemie, 4th edition, volume 9, pages 96–114.

In the Examples which follow, parts are by weight.

EXAMPLE 1

An argon-filled shaking autoclave is charged with a mixture of 8.1 parts of 3-pentenonitrile, 1.4 parts of dicobalt octacarbonyl, 2.6 parts of pyridine, 8 parts of methanol and 30 parts of tetrahydrofuran. The pressure is brought to 140 bars by forcing in carbon monoxide at room temperature. The autoclave is next heated to 160° C; the pressure is then brought to 200 bars by forcing in carbon monoxide, and the reaction mixture is shaken for 4 hours under these conditions. After cooling, and letting down the pressure, the mixture is filtered. Fractional distillation of the reaction mixture gives 9.9 parts of 5-cyanovaleric acid methyl ester (70.1% of theory). Boiling point 118°–120° C/10 mm Hg, $n_D^{20} = 1.4322$.

EXAMPLE 2

If the reaction is carried out as described in Example 1, but with 11.5 parts of ethanol instead of methanol, 10.6 parts of 5-cyanovaleric acid ethyl ester (68.3% of theory) of boiling point 126°–129° C/10 mm Hg, $n_D^{20} = 1.4340$, are obtained.

EXAMPLE 3

A mixture of 8.1 parts of 4-pentenonitrile, 1.4 parts of dicobalt octacarbonyl, 2.6 parts of pyridine, 8 parts of methanol and 30 parts of acetone is reacted in the same way as in Example 1. The pressure is brought to 200 bars by forcing in carbon monoxide at room temperature. The autoclave is heated to 160° C, the pressure is raised to 300 bars by forcing in further carbon monoxide, and the autoclave is shaken for two hours under these conditions. Fractional distillation of the material discharged from the autoclave gives 10.6 parts of 5-cyanovaleric acid methyl ester (75.1% of theory); boiling point 122°–124° C/11 mm Hg.

EXAMPLE 4

If, in Example 1, dicobalt octacarbonyl is replaced by 2 parts of cobalt acetate tetrahydrate, and the reaction is carried out under the same conditions, 9.1 parts of 5-cyanovaleric acid methyl ester (64.5% of theory) are obtained; boiling point 122°–124° C/11 mm Hg.

EXAMPLE 5

If the reaction is carried out as described in Example 1, without acetone, and with 50 parts of methanol instead of 8 parts, at 170° C and 300 bars pressure, 7.8 parts of 5-cyanovaleric acid methyl ester (55.3% of theory) are obtained; boiling point 122°–124° C/11 mm Hg.

EXAMPLE 6

The acetone in Example 1 is replaced by 30 parts of toluene. The pressure is first brought to 200 bars at room temperature by forcing in carbon monoxide and the mixture is then heated to 140° C. The pressure is then raised to 300 bars by forcing in carbon monoxide and the reaction mixture is shaken under these conditions for 20 hours. Following the procedure described in Example 1, 8.4 parts of 5-cyanovaleric acid methyl ester (59.5% of theory) of boiling point 122°–124° C/11 mm Hg are obtained.

EXAMPLE 7

If the procedure described in Example 4 is followed, but at 200° C, 4.7 parts of 5-cyanovaleric acid methyl ester (33.3% of theory) of boiling point 122°–124° C/11 mm Hg are obtained.

EXAMPLE 8

If the procedure described in Example 1 is followed, with 0.35 part of dicobalt octacarbonyl instead of 1.4 parts, and with 60 parts of dimethoxyethane in place of 30 parts of tetrahydrofuran, 8.4 parts of 5-cyanovaleric acid methyl ester (59.5% of theory) of boiling point 122°–124° C/11 mm Hg are obtained.

EXAMPLE 9

The procedure described in Example 1 is followed, but using 60 parts of acetone instead of 30 parts of tetrahydrofuran, and bringing the pressure initially to 400 bars by forcing in carbon monoxide at room temperature. The mixture is then heated to 160° C and the pressure is increased to 600 bars by forcing in carbon monoxide. After a residence time of 4 hours under these conditions, 6.5 parts of 5-cyanovaleric acid methyl ester (46% of theory) of boiling point 122°–124° C/11 mm Hg are obtained by the method described in Example 1.

EXAMPLE 10

Pyridine is replaced by 4.1 parts of isoquinoline in the reaction described in Example 1, but in other respects the conditions described there are followed. 6.4 parts (45.3% of theory) of 5-cyanovaleric acid methyl ester are obtained. Boiling point 119°–121° C/10 mm Hg.

EXAMPLE 11

If pyridine is replaced by 3.1 parts of 4-methylpyridine in the reaction described in Example 1, and in other respects the conditions there are followed, 8.1 parts of 5-cyanovaleric acid methyl ester (57.4% of theory) are obtained; boiling point 118°–121° C/10 mm Hg.

EXAMPLE 12

Example 3 is carried out with an equal amount of 3-pentenonitrile in place of 4-pentenonitrile, and with the methanol replaced by 32.6 parts of 2-ethylhexanol. The pressure is brought to 200 bars by forcing in carbon monoxide. The mixture is heated to 160° C, the pressure is raised to 260 bars by forcing in further carbon monoxide, and the autoclave is shaken for 4 hours under these conditions. After distillation, 11.7 parts of 5-cyanovaleric acid 2-ethylhexyl ester (48.9% of theory) are obtained; boiling point 136°–140° C/1 mm Hg, $n_D^{20} = 1.4470$.

EXAMPLE 13

Example 3 is carried out with an equal amount of 3-pentenonitrile in place of 4-pentenonitrile, and with the methanol replaced by 25 parts of cyclohexanol, the mixture is heated to 160° C, and the autoclave is shaken for 4 hours, under a final pressure of 260 bars. 9.9 parts of 5-cyanovaleric acid cyclohexyl ester (47.3% of theory) of boiling point 124.5°–125.5° C/0.5 mm Hg, $n_D^{20}$ = 1.4598, are obtained.

EXAMPLE 14

0.9 part of water is added to the starting mixture described in Example 1, and in other respects the same conditions are used. By following the method described in Example 1, 8.1 parts of 5-cyanovaleric acid methyl ester (57.4% of theory) of boiling point 122°–124° C/11 mm Hg are obtained.

EXAMPLE 15

If the reaction is carried out as described in Example 1, with 18 parts of isopropanol instead of methanol, 11 parts of 5-cyanovaleric acid isopropyl ester (65% of theory) are obtained; boiling point 138°–140° C/15 mm Hg, $n_D^{20}$ = 1.4300.

EXAMPLE 16

Methanol is replaced by 4.5 parts of water in the reaction charge described in Example 1. The carbonylation is carried out under the same conditions as there. Air is passed through the reaction mixture obtained after cooling and letting down the pressure. After stripping off the constituents which are volatile at 50° C on a rotary evaporator under reduced pressure, water is added to the residue and the mixture is acidified with sulfuric acid and repeatedly extracted with ether. The combined ether extracts are subjected to fractional distillation. 7.8 parts of 5-cyanovaleric acid (61.4% of theory) are obtained; boiling point 129°–133° C/0.7–0.8 mm Hg.

We claim:

1. A process for the manufacture of 5-cyanovaleric acid and its esters by reaction of alkenyl-nitriles with carbon monoxide and hydroxyl-containing compounds at elevated temperature and elevated pressure in the presence of metal carbonyls and basic compounds, said process being carried out by effecting the reaction without adding hydrogen, wherein a pentenonitrile of the formula

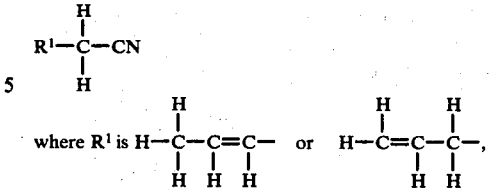

where $R^1$ is $$H-\underset{\underset{H}{|}}{\overset{\overset{H}{|}}{C}}-C=C- \quad \text{or} \quad H-C=C-\underset{\underset{H}{|}}{\overset{\overset{H}{|}}{C}}-,$$

is reacted with carbon monoxide and a compound, containing a hydroxyl group, of the formula $$R^2-OH \qquad \text{II}$$

where $R^2$ is alkyl of 1 to 12 carbon atoms which may be substituted by 1 or 2 hydroxyl groups, cycloalkyl of 5 to 7 carbon atoms, aralkyl of 7 to 12 carbon atoms, phenyl or hydrogen, the above radicals may be further substituted by alkyl or alkoxy each of 1 to 4 carbon atoms, or hydroxy, at a temperature of from 140° to 300° C and a pressure of from 100 to 700 bars, in the presence of pure carbonyls and/or carbonyls of which the carbon monoxide is partially replaced by neutral or charged ligands and/or carbonyl hydrides of iridium, iron, nickel, ruthenium, rhodium and/or cobalt and basic heterocyclic compounds, said basic heterocyclic compound being a 5-membered or 6-membered nitrogen-containing ring which is unsubstituted or substituted by alkyl or alkoxy each of 1 to 4 carbon atoms, or hydroxyl, to each of which rings one or 2 aromatic nuclei, which may be substituted by the above substituents, may be fused.

2. A process as claimed in claim 1, wherein the reaction is carried out with a ratio of from 1 to 10 moles of water or of alcohol II per mole of pentenonitrile I.

3. A process as claimed in claim 1, wherein the reaction is carried out with organic solvents which are inert under the reaction conditions.

4. A process as claimed in claim 1, wherein the reaction is carried out at from 140° to 250° C.

5. A process as claimed in claim 1, wherein the reaction is carried out under a pressure of from 160 to 300 bars.

6. A process as claimed in claim 1, wherein the reaction is carried out with from 10 to 50 moles of carbon monoxide per mole of starting material I.

7. A process as claimed in claim 1, wherein the reaction is carried out with from 0.1 to 2 moles of heterocyclic compound per mole of starting material I.

8. A process as claimed in claim 1, wherein the reaction is carried out with from 0.005 to 0.1 mole of carbonyl compound per mole of starting material I.

9. A process as claimed in claim 1, wherein the reaction is carried out with $Fe(CO)_5$, $Ni(CO)_4$, $Ru(CO)_5$, $Rh_2(CO)_8$, $Ir_2(CO)_8$, $((C_6H_5)_3P)_2Ni(CO)_2$, $((C_6H_5)_3P)Fe(CO)_4$, $Ni(CN-C_6H_5)_4$, $K_2Ni(CO)_2(CN)_2$, $Ir(CO)_2Br_2$, $HCo(CO)_4$, $H_2Fe(CO)_4$, $HRh(CO)_4$ and/or dicobalt octacarbonyl $Co_2(CO)_8$.

* * * * *